United States Patent
Yu et al.

(10) Patent No.: US 11,773,370 B2
(45) Date of Patent: Oct. 3, 2023

(54) STEM CELL-DERIVED SKIN PRECURSOR CELL CULTURE MEDIUM AND PREPARATION METHOD THEREFOR

(71) Applicant: CHA BIOTECH CO., LTD., Gangnam-gu (KR)

(72) Inventors: Ji Min Yu, Seongnam-si (KR); Ae Ri Kim, Seongnam-si (KR)

(73) Assignee: CHA BIOTECH CO., LTD., Gangnam-gu (KR)

( * ) Notice: Subject to any disclaimer, the term of this patent is extended or adjusted under 35 U.S.C. 154(b) by 643 days.

(21) Appl. No.: 16/627,671

(22) PCT Filed: Jul. 2, 2018

(86) PCT No.: PCT/KR2018/007470
§ 371 (c)(1),
(2) Date: Dec. 30, 2019

(87) PCT Pub. No.: WO2019/004800
PCT Pub. Date: Jan. 3, 2019

(65) Prior Publication Data
US 2020/0157500 A1 May 21, 2020

(30) Foreign Application Priority Data
Jun. 30, 2017 (KR) ........................ 10-2017-0083861

(51) Int. Cl.
*C12N 5/071* (2010.01)
*C12N 5/00* (2006.01)
*C12P 21/02* (2006.01)

(52) U.S. Cl.
CPC ............ *C12N 5/0625* (2013.01); *C12P 21/02* (2013.01); *C12N 2500/38* (2013.01); *C12N 2500/90* (2013.01); *C12N 2501/17* (2013.01); *C12N 2501/20* (2013.01); *C12N 2501/39* (2013.01); *C12N 2501/998* (2013.01); *C12N 2501/999* (2013.01); *C12N 2506/02* (2013.01); *C12N 2506/025* (2013.01); *C12N 2506/03* (2013.01)

(58) Field of Classification Search
CPC .............. C12N 5/0625; C12N 2500/38; C12N 2500/90; C12N 2501/39; C12N 2506/025
See application file for complete search history.

(56) References Cited

U.S. PATENT DOCUMENTS

| 9,708,584 B2 | 7/2017 | Kang et al. |
| 2015/0118748 A1 | 4/2015 | Ra et al. |
| 2016/0102289 A1* | 4/2016 | Yu .......................... A61P 43/00 435/405 |

FOREIGN PATENT DOCUMENTS

| KR | 10-1830062 B1 | 2/2018 | |
| WO | WO-2008070868 A1 * | 6/2008 | ............ A61K 31/05 |
| WO | WO 2013/081436 A1 | 6/2013 | |
| WO | WO 2014/003319 A1 | 1/2014 | |
| WO | WO 2016/039687 A1 | 3/2016 | |
| WO | WO 2016/061071 A1 | 4/2016 | |

OTHER PUBLICATIONS

Aberdam. Derivation of keratinocyte progenitor cells and skin formation from embryonic stem cells. Int. J. Dev. Biol. 48: 203-206 (Year: 2004).*
Averdam et al. Derivation of keratinocyte progenitor cells and skin formation from embryonic stem cells. Int. J. Dev. Biol. 48: 203-206 (Year: 2004).*
Bilousova et al. Differentiation of Mouse Induced Pluripotent Stem Cells into a Multipotent Keratinocyte Lineage. Journal of Investigative Dermatology (2011) 131, 857-864 (Year: 2011).*
Kim et al. A comparative analysis of their potential as placenta-derived stem cells. Cell Tissue Res. 2011;346:53-64 (Year: 2011).*
Ma et al. Differentiation of bone marrow-derived mesenchymal stem cells into multi-layered epidermis-like cells in 3D organotypic coculture. Biomaterials 30 (2009) 3251-3258 (Year: 2009).*
Schneider et al. Long-term survival and characterisation of human umbilical cord-derived mesenchymal stem cells on dermal equivalents. Differentiation 79(2010)182-193 (Year: 2010).*
Japanese Office Action dated Feb. 24, 2021 in Japanese Patent Application No. 2020-500191 (with English translation), 6 pages.

(Continued)

*Primary Examiner* — Taeyoon Kim
(74) *Attorney, Agent, or Firm* — Oblon, McClelland, Maier & Neustadt, L.L.P.

(57) ABSTRACT

Provided are a method of preparing a stem cell-derived epidermal progenitor cell conditioned medium, the method including: differentiating stem cells to stem cell-derived epidermal progenitor cells by culturing the stem cells in a differentiation medium containing ascorbic acid and hydrocortisone; producing a culture of stem cell-derived epidermal progenitor cells by culturing the differentiated stem cell-derived epidermal progenitor cells in a medium; and recovering the stem cell-derived epidermal progenitor cell conditioned medium from the culture of the stem cell-derived epidermal progenitor cells, a stem cell-derived epidermal progenitor cell conditioned medium prepared by the method, and a method of producing a protein from stem cell-derived epidermal progenitor cells, the method including the method of preparing the stem cell-derived epidermal progenitor cell conditioned medium.

13 Claims, 4 Drawing Sheets
Specification includes a Sequence Listing.

(56) References Cited

OTHER PUBLICATIONS

Yasuyuki Fujita, et al., "Vascular and Tissue Regeneration by CD34+ Cells" Pediatric Cardiology and Cardiac Surgery, vol. 31, No. 3, 2015, pp. 80-87.
Russian Office Action and Search Report dated Aug. 7, 2020 in Russian Patent Application No. 2020103760/10(005753) (with English language translation), 12 pages.
Singaporean Search Report dated Nov. 23, 2020 in Singaporean Patent Application No. 11201913778V, 8 pages.
International Search Report dated Apr. 3, 2019 in PCT/KR2018/007470 filed on Jul. 2, 2018, 2 pages.
Korean Office Action dated Aug. 13, 2018 in Korean Patent Application No. 10-2017-0083861 filed on Jun. 30, 2017, 6 pages.
Korean Office Action dated Feb. 22, 2019 in Korean Patent Application No. 10-2017-0083861 filed on Jun. 30, 2017, 6 pages.
Korean Office Action dated Apr. 18, 2019 in Korean Patent Application No. 10-2017-0083861 filed on Jun. 30, 2017, 5 pages.
Couteaudier, M. et al, "Derivation of keratinocytes from chicken embryonic stem cells: Establishment and characterization of differentiated proliferative cell populations," Stem Cell Research, vol. 14, No. 2, 2015, pp. 224-237.
Shim, J.H. et al, "Human Dermal Stem/Progenitor Cell-Derived Conditioned Medium Ameliorates Ultraviolet A-Induced Damage of Normal Human Dermal Fibroblasts," PLoS One, vol. 8, No. 7, e67604, Jul. 2013, pp. 1-9.
Yavari, K. et al, "Human Umbilical Cord Blood Stem Cells Differentiate into Keratinocytes under In Vitro Conditions and Culturing Differentiated Cells on Bacterial Cellulose Film," International Journal of Stem Cell Research and Transplantation (IJST), vol. 4, No. 7, 2016, pp. 216-219.
Sohn, S. et al, "(149) The protective effects of stem cell-derived epidermal progenitor cell-conditioned media against oxidative stress in human dermal fibroblasts," Europe Society of Dermal Research (ESDR) Presentation, 2016, total pages: 1.
Nair, R.P. et al, "Identification of p63 keratinocyte progenitor cells in circulation and their matrix-directed differentiation to epithelial cells," Stem Cell Research & Therapy, vol. 4, No. 2, 38, 2013, pp. 1-13.
Sohn, S. J. et al, "Anti-aging Properties of Conditioned Media of Epidermal Progenitor Cells Derived from Mesenchymal Stem Cells," Dermatology and Therapy, vol. 8, 2018, pp. 229-244.
Japanese Office Action dated Oct. 12, 2021 in Japanese Patent Appiication No. 2020-500191 (with English translation), 8 pages.
Liu, S., et al., "Epidermal Development in Mammals: Key Regulators, Signals from Beneath, and Stem Cells", International Journal of Molecular Sciences, vol. 14, 2013, pp. 10869-10895.
Office Action dated May 24, 2022 in Japanese Patent Application No. 2020-500191 (with English translation), 5 pages.
Written Opinion dated Jul. 24, 2022 in Singaporean Patent Application No. 11201913778V, 7 pages.

* cited by examiner

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer for Krt5

<400> SEQUENCE: 1
gtctcgccag tcaagtgtgt                                              20

<210> SEQ ID NO 2
<211> LENGTH: 18
<212> TYPE: DNA
<213> ORGANISM: Artificial Sequence
<220> FEATURE:
<223> OTHER INFORMATION: Reverse primer for Krt5

<400> SEQUENCE: 2
gacacggagg tgaagctg                                                18

<210> SEQ ID NO 3
<211> LENGTH: 20
<212> TYPE: DNA
<213> ORGANISM: Artificial Sequence
<220> FEATURE:
<223> OTHER INFORMATION: Forward primer for Krt1

<400> SEQUENCE: 3
gggtggttat ggtcctgtct                                              20

<210> SEQ ID NO 4
<211> LENGTH: 20
<212> TYPE: DNA
```

```
<213> ORGANISM: Artificial Sequence
<220> FEATURE:
<223> OTHER INFORMATION: Reverse primer for Krt1

<400> SEQUENCE: 4
ggatctcagg gtcaatctcc                                              20

<210> SEQ ID NO 5
<211> LENGTH: 20
<212> TYPE: DNA
<213> ORGANISM: Artificial Sequence
<220> FEATURE:
<223> OTHER INFORMATION: Forward primer for IVL

<400> SEQUENCE: 5
ccaggtccaa gacattcaac                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for IVL

<400> SEQUENCE: 6
actgcgggtg gttatttatg                                              20

<210> SEQ ID NO 7
<211> LENGTH: 19
<212> TYPE: DNA
<213> ORGANISM: Artificial Sequence
<220> FEATURE:
<223> OTHER INFORMATION: FOrward primer for Krt14

<400> SEQUENCE: 7
gagcagcaga accaggagt                                               19

<210> SEQ ID NO 8
<211> LENGTH: 20
<212> TYPE: DNA
<213> ORGANISM: Artificial Sequence
<220> FEATURE:
<223> OTHER INFORMATION: Reverse primer for Krt14

<400> SEQUENCE: 8
gagaactggg aggaggagag                                              20

<210> SEQ ID NO 9
<211> LENGTH: 20
<212> TYPE: DNA
<213> ORGANISM: Artificial Sequence
<220> FEATURE:
<223> OTHER INFORMATION: Forward primer for Krt10

<400> SEQUENCE: 9
actactcttc ctcccgcagt                                              20

<210> SEQ ID NO 10
<211> LENGTH: 20
<212> TYPE: DNA
<213> ORGANISM: Artificial Sequence
```

```
<220> FEATURE:
<223> OTHER INFORMATION: Reverse primer for Krt10

<400> SEQUENCE: 10
tgagctaaat cctccaccaa                                              20
```

STEM CELL-DERIVED SKIN PRECURSOR CELL CULTURE MEDIUM AND PREPARATION METHOD THEREFOR

TECHNICAL FIELD

The present disclosure relates to a method of preparing a stem cell-derived epidermal progenitor cell conditioned medium, a stem cell-derived epidermal progenitor cell conditioned medium prepared by the method, and a method of producing a protein from stem cell-derived epidermal progenitor cells.

BACKGROUND ART

Stem cells having pluripotent properties can differentiate to specific cells, and are be divided into embryonic stem cells, adult stem cells, and induced pluripotent stem cells. To date, studies on adult stem cells have been mostly associated with bone marrow, and in some cases, the studies cover methods of isolating and culturing stem cells from adipose tissues or cord blood. Cells in bone marrow and adipose tissues are collected by invasive methods, and in the case of stem cells isolated from middle-age or old-age patients, differentiation potency and proliferation properties thereof are reduced. In addition, in the case of cord blood, cell collection therefrom is easy, but amounts of stem cells in the cord blood are low. Unlike cells derived from bone marrow and fat, cells in umbilical cord (UC) and placenta are isolated from tissues that are already detached from the body, and that is, such cell isolation is carried out in a non-invasive manner. In addition, unlike stem cells derived from embryo, the isolation of the cells in UC and placenta are free from ethical issues. Thus, the cells in UC and placenta have recently been in the spotlight as useful materials for intractability or regenerative medicine, and as primitive cells, the cells may satisfy proliferation capacity and differentiation potency at the same time. In this regard, the cells may be used for tissue regeneration, and may also have advantages to be used after differentiation according to tissue characteristics.

Meanwhile, regarding a cell therapy product, a survival rate thereof after transplantation in the body is not high, and immune rejections may be caused. Thus, examples of extensive and stable success are not easily found in actual clinical applications. In this regard, as an alternative to the cell therapy product, a conditioned cell medium of has been in the spotlight. The conditioned cell medium (also, referred to as a cell medium) is a medium which does not contain cells obtained after culturing cells, but contains various ingredients, such as cytokine, a growth factor, and the like, necessary for cell growth. Such a cell conditioned medium is used to promote cell growth or to isolate specific ingredients, and furthermore, the cell conditioned medium itself is applied to treat various diseases.

The inventors of the present disclosure have established optimal culture conditions to increase an amount of useful proteins, and accordingly, a cell conditioned mediums containing various proteins, which are known to be expressed only in a small amount or not to be expressed in the existing environments for the preparation of a cell conditioned medium, is developed.

DESCRIPTION OF EMBODIMENTS

Technical Problem

Provided is a method of preparing a stem cell-derived epidermal progenitor cell conditioned medium.

Provided is a stem cell-derived epidermal progenitor cell conditioned medium prepared by the method.

Provided is a method of producing a protein from stem cell-derived epidermal progenitor cells.

Solution to Problem

According to an aspect of the present disclosure, provided there is a method of preparing a stem cell-derived epidermal progenitor cell conditioned medium, the method including: differentiating stem cells to stem cell-derived epidermal progenitor cells by culturing the stem cells in a differentiation medium containing ascorbic acid and hydrocortisone; producing a culture of stem cell-derived epidermal progenitor cells by culturing the differentiated stem cell-derived epidermal progenitor cells in a medium; and recovering the stem cell-derived epidermal progenitor cell conditioned medium from the culture of the stem cell-derived epidermal progenitor cells.

The term "stem cell" as used herein refers to a cell having differentiation potency and self-renewal capacity. The stem cell may be divided into a pluripotent stem cell, a multipotent stem cell, and an unipotent stem cell, according to the differentiation ability. The stem cell may include at least one selected from an embryonic stem cell (ESC) (i.e., an inner cell of embryo before implantation), an adult stem cell (i.e., an undifferentiated cell present in tissues and organs), and an induced pluripotent stem cell (i.e., a cell in which dedifferentiation is induced by inserting a gene and/or a protein to a somatic cell, or an induced pluripotent stem cell (iPSC)).

The stem cell may be a mesenchymal stem cell. The term "mesenchymal stem cell (MSC)" as used herein refers to an adult stem cell that has multipotency and self-renewal capacity and excellent proliferativity, and that is genetically stabilized. The MSC is a helper cell for producing fats, cartilages, bones, myeloid epilepsy, muscles, nerves, and the like, and may differentiate to various cells, for example, adipocytes, chondrocytes, skin cells, osteocytes, and the like.

Considering that the stem cell has differentiation potency and self-renewal capacity, types and origins of the stem cell are not limited. The stem cell may be originated from, for example, mammals, humans, monkeys, pigs, horses, cattle, sheep, dogs, cats, mice, rabbits, and the like. The stem cell may be derived from detached umbilical cord, detached placenta, detached fat, detached bone marrow, detached cord blood, or detached amniotic fluid. The term "detached" as used herein refers to the presence in an environment that is different from a cellular or tissue environment that naturally occurs.

The term "umbilical cord" as used herein refers to a conduit between a embryo and a pregnant mother to enable a mammalian fetus to grow in placenta, and may be a tissue generally consisting of three vessels, i.e., two umbilical arteries and one umbilical vein, surrounded by Wharton's jelly. The term "placenta" as used herein refers to an organ that develops for a fetus during pregnancy of a mammal, wherein one side of placenta is in contact with a pregnant mother and the other side is in contact with a fetus, and a space therebetween is filled with maternal blood so that a fetus may be supplied with nutrients. Placenta consists of three layers of amnion, chorion, and decidua. Amnion is a clear thin membrane which surrounds a fetus and includes amniotic fluid, and stem cells of a fetus are present in amniotic fluid and/or amnion. Decidua is a membrane formed as a result of a process in which epithelial cells of uterus are modified so that a fertilized egg is implanted in uterus, and stem cells of a pregnant mother are present in decidua. Chorion is a membrane between amnion surrounding a fetus or amniotic fluid and decidua, and develops from a fertilized egg to constitute a part of an egg membrane. Placenta-derived stem cells may be derived from a fetus or a pregnant mother. Amniotic fluid-derived stem cells may be derived from a fetus. Umbilical cord-derived or placenta-derived stem cells are abundant in quantity, proliferate easily, and are capable of differentiating to other cells. The term "bone marrow" as used herein refers to a tissue that produces blood cells including red blood cells, white blood cells, platelets, and the like. The term "cord blood" as used herein refers to blood from umbilical cord of a newborn baby after delivery. The term "fat" as used herein refers to body fat, and stem cells derived from fat are easy to obtain and has a high yield rate by considering that about 1% of adipocytes are estimated to be stem cells.

The method may include obtaining detached umbilical cord, detached placenta, detached fat, detached bone marrow, detached cord blood, or detached amniotic fluid. The detached umbilical cord, the detached placenta, fat, the detached bone marrow, the detached cord blood, or the detached amniotic fluid may be obtained by anatomical methods known in the art. The umbilical cord, the placenta, the amniotic fluid, or the cord blood may each be detached from the body of a pregnant mother after delivery. The detached umbilical cord, the detached placenta, the detached amniotic fluid, or the detached cord blood may be stored in a sterilized container with ice rapidly after the detachment.

The placenta may be, for example, obtained by cutting placental tissues present in the placenta into several sites with sterilized scissors. The placental tissues may include amnion, chorion, or decidua. The umbilical cord may be, for example, obtained by detaching the umbilical cord from the placenta. Then, arteries and vein may be additionally removed from the umbilical cord. The fat may be, for example, obtained by performing liposuction in a subcutaneous fat layer in abdomen or thighs. The placental tissues, the umbilical cord, or the fat may be washed with phosphate buffered saline (PBS) containing antibiotics, such as penicillin, streptomycin, gentamicin, or a combination thereof, once, twice, or three times or more, thereby removing contaminants, such as blood and the like, present in tissues.

The method may include: reacting the detached umbilical cord, the detached placenta, or the detached fat directly with an enzyme; or reacting the detached umbilical cord, the detached placenta, or the detached fat directly with an enzyme after finely cutting the detached umbilical cord, the detached placenta, or the detached fat with sterilized scissors. For example, the detached umbilical cord, the detached placenta, or the detached fat may be finely cut (for example, in a size of about 20 mm or less or about 10 mm or less) with sterilized scissors, and then, cells finely cut therefrom may be reacted with an enzyme.

The method may include obtaining stem cells. The obtaining of the stem cells may be performed by methods known to one of ordinary skill in the art. In the case of the umbilical cord or the placenta, the method may include, for example: adhering the detached umbilical cord or the detached placenta to a culture dish to culture for 5 days to 20 days, 10 days to 20 days, or 10 days to 15 days; confirming cells extending from the cultured umbilical cord or the cultured placenta; and/or reacting a dissociation enzyme with the umbilical cord or the placenta. In one or more embodiment, in the case of the umbilical cord or the placenta, the method may include, for example, reacting a dissociation enzyme with the detached umbilical cord or the detached placenta.

The dissociation enzyme may include collagenase. The term "collagenase" as used herein refers to an enzyme that breaks a peptide bond in collagen, and includes collagenase type I, collagenase type II, collagenase type III, collagenase type IV, or a combination thereof. The dissociation enzyme may include collagenase at a concentration in a range of about 10 U/ml to about 4,000 U/ml, about 20 U/ml to about 2,000 U/ml, about 50 U/ml to about 800 U/ml, about 100 U/ml to about 400 U/ml, or about 150 U/ml to about 300 U/ml, or at a concentration of about 200 U/ml. In addition, the dissociation enzyme may include trypsin, dispase, or a combination thereof. In addition, a solution containing the dissociation enzyme may be water containing collagenase, trypsin, dispase, or a combination thereof, or saline, such as Hank's balanced salt solution (HBSS). The reacting of the dissociation enzyme with the umbilical cord or the placenta may be performed by shake culture or stationary culture. The shake culture or the stationary culture may be performed at a temperature in a range of about 20° C. to about 40° C., about 30° C. to about 40° C., or about 35° C. to about 40° C., or at a temperature of about 37° C., for about 1 hour to about 20 hours, about 2 hours to about 10 hours, about 4 hours to about 9 hours, or about 5 hours to about 6 hours. In the case of the fat, the method may include, for example, include reacting the detached fat with a dissociation enzyme. The dissociation enzyme may include collagenase, trypsin, dispase, or a combination thereof. A solution containing the dissociation enzyme may be water containing collagenase, trypsin, dispase, or a combination thereof, or saline, such as HBSS. The reacting of the fat with the dissociation enzyme may be performed by shake culture or stationary culture.

Additionally, after the reacting of the dissociation enzyme with the umbilical cord, the placenta, or the fat, a process of inactivating the dissociation enzyme may be performed. For example, an enzymatic reaction may be terminated by addition of serum. In addition, after the reacting of the dissociation enzyme with the umbilical cord, the placenta, or the fat, a process of obtaining stem cells from the umbilical cord, the placenta, or the fat may be performed by methods known to one of ordinary skill in the art. For example, after performing centrifugation, a process of isolating cells by using a cell strainer may be performed.

The method may include, before the differentiating of the stem cells to the stem cell-derived epidermal progenitor cells, culturing the stem cells in a serum-containing medium. The serum may be fetal bovine serum (FBS), bovine calf serum (BSC), or a combination thereof. Based on the total volume of the differentiation medium, the serum may be contained by a volume in a range of about 1% to about 50%, about 2% to about 25%, about 5% to about 20%, or about 7.5% to about 12.5%, or by a volume of about 10%. The medium may include fibroblast growth factor-4 (FGF-4) and/or heparin. In the medium, a concentration of FGF-4 may be in a range of about 10 ng/ml to about 40 ng/ml or about 20 ng/ml to about 30 ng/ml, or may be about 25 ng/ml. In the medium, a concentration of heparin may be in a range of about 0.5 μg/ml to about 2 μg/ml or about 0.5 μg/ml to about 1.5 μg/ml, or may be about 1 μg/ml. The may include antibiotics. The antibiotics may include penicillin, streptomycin, gentamicin, or a combination thereof. In the medium, a concentration of the antibiotics may be in a range of about 10 μg/ml to about 250 μg/ml, about 25 μg/ml to about 100 μg/ml, or about 40 μg/ml to about 65 μg/ml, or may be about 50 μg/ml.

The method may include, before the differentiating of the stem cells to the stem cell-derived epidermal progenitor cells, culturing the stem cells in a serum-containing medium for 10 hours to 350 hours. The culturing of the stem cells may be performed for about 10 hours to about 350 hours, about 20 hours to about 170 hours, or about 50 hours to about 70 hours, or for about 0.5 day to about 14 days, about 1 day to about 7 days, or about 2 days to about 3 days. The culturing of the stem cells may be a process of subculturing the isolated stem cells at passage 0 (P0). Here, a passage number of the subculturing is not particularly limited, and may be appropriately selected according to the desired number of prolifering cells. For example, 1 passage to 20 passages, 2 passages to 10 passages, 3 passages to 7 passages, or 4 passages to 5 passages may be performed to obtain required cumulative number of proliferating cells.

The method may include differentiating the stem cells to stem cell-derived epidermal progenitor cells by culturing the stem cells in the differentiation medium containing ascorbic acid and hydrocortisone. In this regard, the stem cells may differentiate to stem cell-derived epidermal progenitor cells as being cultured in the differentiation medium containing ascorbic acid and hydrocortisone.

The term "differentiation" as used herein refers to a phenomenon in which structures of functions of cells are specialized to one another during division and proliferation of cells, and in other words, cells or tissues of living things change shapes or functions to perform tasks given thereto. Measuring or determining the degree of differentiation to particular cell types may be performed by methods well known in the art. In addition, the differentiation may be confirmed by: measuring changes in cell surface markers (for example, in a way of staining cells with tissue-specific or cell-specific antibiotics) and cell morphology using techniques such as flow cytometry or immunocytochemistry; examining cell morphology using an optical microscope or a confocal microscope; or measuring changes in gene expression using techniques well known in the art such as polymerase chain reaction (PCR) and gene-expression profiles.

The stem cells may have different behaviors including cell division, differentiation, or migration, according to the surrounding microenvironment (e.g., stem cell niche). The stem cells may also have different behaviors in gene expression by stimulation from the surrounding microenvironment, and accordingly, cells to be differentiated may be changed.

The differentiation medium may include ascorbic acid and hydrocortisone. Ascorbic acid is an organic compound having antioxidant properties, is one type of vitamin C, is water-soluble, and has a molecular formula of $C_6H_8O_6$. Ascorbic acid may be L-ascorbic acid. Ascorbic acid may be in the form of ascorbic acid or a salt thereof. The salt of ascorbic acid may be an inorganic salt, an alkali metal salt, or an alkaline earth metal salt. For example, the salt of ascorbic acid may be an inorganic salt, such as hydrochloride, nitrate, sulfate, and the like, an alkali metal salt, such as sodium salt, potassium salt, calcium salt, magnesium salt, and the like, or an alkaline earth metal salt. For example, the salt of ascorbic acid may be a salt of L-ascorbic acid, such as sodium L-ascorbic acid, magnesium of L-ascorbic acid, potassium of L-ascorbic acid, calcium of L-ascorbic acid, and the like. Ascorbic acid may influence proliferation and basement membrane formation of the stem cell-derived epidermal progenitor cells. In the medium, a concentration of ascorbic acid may be in a range of about 0.03 μM to about 3 μM, about 0.05 μM to about 2 μM, about 0.1 μM to about 1 μM, or about 0.1 μM to about 0.5 μM.

Hydrocortisone is one type of adrenocortical hormones and has a molecular formula of $C_{21}H_{30}O_5$. Hydrocortisone may be in the form of hydrocortisone or a salt thereof. The salt of hydrocortisone may be an acid addition salt. For example, the salt of hydrocortisone may be an inorganic acid salt of hydrochloric acid, nitric acid, phosphoric acid, sulfuric acid, hydrobromic acid, hydroiodic acid, nitrous acid, phosphorous acid, and the like, or a non-toxic organic acid, such as aliphatic monocarboxylate and dicarboxylate, phenyl-substituted alkanoate, hydroxy alkanoate and alkandioate, aromatic acid, aliphatic and aromatic sulfonic acid, and the like. Hydrocortisone, which is a factor stimulating the differentiation potency to epidermal progenitor cells, plays a small role in lipid synthesis and plasma membrane formation, and may also promote formation of stratum corneum which is located above an epidermal layer. In the medium, a concentration of hydrocortisone may be in a range of about 0.05 μg/ml to about 5 μg/ml, about 0.075 μg/ml to about 3.5 μg/ml, about 0.1 μg/ml to about 2.5 μg/ml, about 0.2 μg/ml to about 1.25 μg/ml, about 0.3 μg/ml to about 1 μg/ml, or about 0.4 μg/ml to about 0.6 μg/ml.

The differentiation medium is not particularly limited as long as it can be used for cell culture, and for example, the differentiation medium may include at least one selected from Dulbecco's Modified Eagle's Medium (DMEM), Minimal Essential Medium (MEM), Basal Medium Eagle (BME), RPMI 1640, F-10, F-12, DMEM/F12, α-Minimal Essential Medium (α-MEM), Glasgow's Minimal Essential Medium (G-MEM), Iscove's Modified Dulbecco's Medium (IMDM), MacCoy's 5A medium, AmnioMax complete medium, AmnioMax□ complete medium, EBM-2 Basal medium, Chang's Medium, and MesenCult-XF. The differentiation medium may be a serum-containing medium. The serum may be FBS, BSC, or a combination thereof. Based on the total volume of the differentiation medium, the serum may be contained by a volume in a range of about 1% to about 50%, about 2% to about 25%, about 5% to about 20%, or about 7.5% to about 12.5%.

The method may include differentiating the stem cells to the stem cell-derived epidermal progenitor cells by culturing the stem cells in the differentiation medium for about 120 hours to about 600 hours, about 150 hours to about 500 hours, about 180 hours to about 450 hours, or about 200 hours to about 300 hours, or for about 5 days to about 25 days, about 6 days to about 21 days, or about 7 days to about 18 hours, for about 8 hours to about 15 days, or about 9 days to about 12 hours.

The skin consists of an epidermal layer, a dermal layer, and a subcutaneous fat layer. At the most bottom part of the epidermal layer, a base layer is located, and new epidermal cells (also referred to as keratinocytes, skin tissue cells, or keratinocytes) are formed in the base layer through cell division, and the formed epidermal cells continuously replace dead cells above the epidermal layer. Such a process induces regeneration of skin cells. The stem cell-derived epidermal progenitor cells may constitute the epidermal layer, for example, the base layer. The stem cell-derived epidermal progenitor cells may be progenitor cells of the keratinocyte.

The stem cell-derived epidermal progenitor cells may have limited differentiation potency and limited self-renewal capacity compared to the stem cells. For example, the stem cell-derived epidermal progenitor cells may be converted to cells having the differentiation potency of 100%, cells having the differentiation potency of 0% from stem cells having the differentiation potency of any %, or cells having the differentiation potency lower than any %. The stem cell-derived epidermal progenitor cells may be used interchangeably with stem cell-derived epidermal progenitor cells, differentiated skin progenitor cells, differentiated epidermal stem cells, skin stem cells, or epidermal stem cells.

In the stem cell-derived epidermal progenitor cells, expression of at least one selected from kerain 5 (Krt5), keratin 1 (Krt1), and keratin 14 (Krt14) may be increased, as compared to the expression in the stem cells before the culture in the differentiation medium. That is, as the stem cells differentiate to the epidermal progenitor cells, the expression of at least one selected from Krt5, Krt1, and Krt14 may be increased. The increase may indicate an increase in the expression of genes, i.e., an amount of mRNA or proteins, as much as at least two times, at least 4 times, at least 8 times, at least 10 times, or at least 20 times or higher. The stem cell-derived epidermal progenitor cells may be differentiated without reaching the late stage of the differentiation in which a large amount of Krt10 and/or involucres (IVL) is expressed depending on the degree of the differentiation. The expression may be confirmed by measuring changes in the gene expression using techniques such as real-time PCR (RT-PCR) or immunoblot (IB). The stem cell-derived epidermal progenitor cells may represent a specific shape of a circle in a constant size.

The method may include producing a culture of the stem cell-derived epidermal progenitor cells by culturing the differentiated stem cell-derived epidermal progenitor cells.

The culturing may be performed by culturing the differentiated stem cell-derived epidermal progenitor cells without passage subculture in the medium. The medium may be suitable for production of proteins, and in the medium, useful proteins may be produced and secreted out of cells through intercellular interactions during the culture of the differentiated stem cell-derived epidermal progenitor cells. The medium may be a serum-free medium. The medium may not include choline chloride, phenol red (or phenolsulfoophthalein), or a combination thereof. The medium is not particularly limited as long as it can be used for cell culture, and for example, the medium may include at least one selected from DMEM, MEM, BME, RPMI 1640, F-10, F-12, DMEM/F12, α-MEM, G-MEM, IMDM, MacCoy's 5A medium, AmnioMax complete medium, AminoMax☐ complete medium, EBM-2 Basal medium, Chang's Medium, and MesenCult-XF.

The method may include producing a culture of the stem cell-derived epidermal progenitor cells by culturing the differentiated stem cell-derived epidermal progenitor cells in the medium for about 10 hours to about 350 hours, about 15 hours to about 200 hours, about 20 hours to about 170 hours, or about 40 hours to about 80 hours, or for about 0.5 day to about 15 days, about 1 day to about 8 days, about 1.5 days to about 4 days, or about 2 days to about 3 days.

The culture of the stem cell-derived epidermal progenitor cells may refer to the medium, the differentiated epidermal progenitor cells, or a mixture thereof, obtained during or after culturing the differentiated epidermal progenitor cells in the medium.

The differentiated stem cell-derived epidermal progenitor cell may secrete epidermal progenitor cell-derived proteins out of the cells through intercellular interactions while being cultured in the medium. The stem cell-derived epidermal progenitor cells may have different behaviors in the gene expression by stimulation from the surrounding environments, and accordingly, types and amounts of proteins secreted from the stem cell-derived epidermal progenitor cells may also vary. The stimulation may include a medium in which the stem cell-derived epidermal progenitor cells are cultured, and/or a culture time. That is, depending on a culture medium and/or a culture time, types and amounts of proteins secreted from the stem cell-derived epidermal progenitor cells may vary, and compositions and amounts of proteins present in the stem cell-derived epidermal progenitor conditioned medium may also vary.

The method may include recovering the stem cell-derived epidermal progenitor cell conditioned medium from the culture of the stem cell-derived epidermal progenitor cells. The recovery may be to obtain the culture of the stem cell-derived epidermal progenitor cells or a supernatant thereof, which is obtained during or after culturing the differentiated epidermal progenitor cells in the medium. The recovery may be to obtain the culture of the stem cell-derived epidermal progenitor cells or a supernatant thereof, which is obtained during or after culturing the differentiated stem cell-derived epidermal progenitor cells in the medium, after removing the differentiated epidermal progenitor cells and/or macromolecules by centrifugation or filtration through a filter.

The stem cell-derived epidermal progenitor cell conditioned medium may include proteins secreted out of the cells by the stem cell-derived epidermal progenitor cells. The stem cell-derived epidermal progenitor cells may produce and secrete proteins as being cultured in the medium. Such proteins may include useful proteins, such as cytokines, growth factors, and the like. The stem cell-derived epidermal progenitor cell conditioned medium may include proteins listed in FIG. 5. The stem cell-derived epidermal progenitor cell conditioned medium may include at least one selected from thrombospondin (TSP), tissue inhibitor of metalloproteinases 2 (TIMP2), tissue inhibitor of metalloproteinases 1 (TIMP1), ectodysplasin-A2 (EDA-A2), X-linked ectodysplasin-A receptor (XEDAR), angiopoietin-1, secreted protein acidic and rich in cysteine (SPARC), transmembrane protein with EGF-like and two follistatin-like domains 1/tomoregulin-1 (TMEFF1/Tomoregulin-1), nidogen-1, insulin-like growth factor-binding protein-3 (IGFBP-3), thrombospondin-2, TNF-related activation-induced cytokine (TRANCE), and interleukin-15 receptor alpha (IL-15R alpha).

The stem cell-derived epidermal progenitor cell conditioned medium may include at least one selected from TSP, TIMP1, TIMP2, EDA-A2, XEDAR, angiopoietin-1, SPARC, TMEFF1/Tomoregulin-1, nidogen-1, IGFBP-3, thrombospondin-2, TRANCE, and IL-15R alpha), at a concentration of about 10 pg/ml or more, about 15 pg/ml or more, or about 20 pg/ml or more.

The stem cell-derived epidermal progenitor cell conditioned medium may include at least one selected from groucho (GRO), latent TGF-beta binding protein 1 (latent TGF-beta bp1), crossveinless-2 (CV-2), Smad 4, interleukin-8 (IL-8), Activin C, interleukin-6 (IL-6), macrophage inflammatory protein 2 (MIP2), and Activin A.

When culturing, in the medium, the differentiated epidermal progenitor cells obtained by culturing the stem cells in the differentiation medium to differentiate to the epidermal progenitor cells, an amount of useful proteins present in the cell culture and/or among cell-derived proteins may be increased, as compared to a case where cells obtained by culturing the stem cells in a medium containing no ascorbic acid and hydrocortisone are cultured in a medium or a case where typical epidermal progenitor cells are cultured in a medium. The increased amount may be confirmed by measuring changes in the gene expression behaviors using techniques such as RT-PCR, IB, enzyme-linked immunosorbent assay (ELISA), and the like.

According to another aspect of the present disclosure, provided there is a stem cell-derived epidermal progenitor cell conditioned medium produced by a method of preparing a stem cell-derived epidermal progenitor cell conditioned medium, the method including: differentiating stem cells to stem cell-derived epidermal progenitor cells by culturing the stem cells in a differentiation medium containing ascorbic acid and hydrocortisone; producing a culture of stem cell-derived epidermal progenitor cells by culturing the differentiated stem cell-derived epidermal progenitor cells in a medium; and recovering the stem cell-derived epidermal progenitor cell conditioned medium from the culture of the stem cell-derived epidermal progenitor cells.

The stem cell-derived epidermal progenitor cell conditioned medium may include proteins secreted out of the cells by the stem cell-derived epidermal progenitor cells, and may include proteins listed in FIG. 5. The stem cell-derived epidermal progenitor cell conditioned medium may include at least one selected from TSP, TIMP1, TIMP2, EDA-A2, XEDAR, Angiopoietin-1, SPARC, TMEFF1/Tomoregulin-1, Nidogen-1, IGFBP-3, Thrombospondin-2, TRANCE, and IL-15R alpha.

The stem cell-derived epidermal progenitor cell conditioned medium may be a conditioned medium obtained after culturing the differentiated stem cell-derived epidermal progenitor cells in the medium, and may include proteins secreted out of the cells through intercellular interactions during the culture of the differentiated stem cell-derived epidermal progenitor cells. Such proteins may include useful proteins, such as cytokines, growth factors, and the like. The stem cell-derived epidermal progenitor cell conditioned medium produced by the method of preparing the stem cell-derived epidermal progenitor cell conditioned medium may include a number of useful proteins at high concentrations, and according to the method of preparing the stem cell-derived epidermal progenitor cell conditioned medium, even when the above process is repeatedly performed, the stem cell-derived epidermal progenitor cell conditioned medium including useful proteins in a constant composition and at a constant concentration may be obtained.

According to an aspect of the present disclosure, provided there is a method of producing a protein from stem cell-derived epidermal progenitor cells, the method including: differentiating stem cells to stem cell-derived epidermal progenitor cells by culturing the stem cells in a differentiation medium containing ascorbic acid and hydrocortisone; producing a culture of stem cell-derived epidermal progenitor cells by culturing the differentiated stem cell-derived epidermal progenitor cells in a medium; and recovering the stem cell-derived epidermal progenitor cell conditioned medium from the culture of the stem cell-derived epidermal progenitor cells.

The differentiating of the stem cells to the stem cell-derived epidermal progenitor cells by culturing the stem cells in the differentiation medium containing ascorbic acid and hydrocortisone; the producing of the culture of the stem cell-derived epidermal progenitor cells by culturing the differentiated stem cell-derived epidermal progenitor cells in the medium; and the recovering of the stem cell-derived epidermal progenitor cell conditioned medium from the culture of the stem cell-derived epidermal progenitor cells may each be understood by referring to the corresponding descriptions thereof provided herein.

The protein produced from the stem cell-derived epidermal progenitor cells may include a useful protein secreted out of the cells through intercellular interactions during the culture of the differentiated stem cell-derived epidermal progenitor cells in the medium. Such a protein may include a useful protein, such as cytokines, growth factors, and the like. The protein produced by the method of producing the protein from the stem cell-derived epidermal progenitor cells may include a large number of the useful protein at a high concentration, and according to the method of producing the protein, even when the process above is repeatedly performed, the protein including the useful protein in a constant composition and at a constant concentration may be obtained. In addition, according to the method of producing the protein from the stem cell-derived epidermal progenitor cell, a large number of the useful protein may be produced in a large quantity.

Advantageous Effects of Disclosure

Referring to a method of preparing a conditioned medium of a stem cell-derived skin progenitor cell according to one aspect and a conditioned medium of a stem cell-derived skin progenitor cell produced by the method, a large amount of useful proteins may be contained in the conditioned medium of the stem cell-derived skin progenitor cell.

MODE OF DISCLOSURE

Hereinafter, the present disclosure will be described in detail with reference to Examples. However, Examples are for illustrative purposes only, and the scope of the present disclosure is not limited to Examples.

EXAMPLE 1

Preparation of Conditioned Medium of Stem Cell-Derived Epidermal Progenitor Cell and Identification of Protein Produced from Stem Cell-Derived Epidermal Progenitor Cell 1. Preparation of Conditioned Medium of Stem Cell-Derived Epidermal Progenitor Cell (1) Differentiation of Stem Cell into Epidermal Progenitor Cell An informed consent based on sufficient explanation in advance was received from a healthy mother who had delivered normally, and the umbilical cord was detached from the placenta collected at normal placental delivery. Each of the detached placenta and the detached umbilical cord was washed twice to five times with dulbecco's phosphate-buffered saline (DPBS) containing no Ca/Mg to remove blood therefrom. Then, the placental tissue was cut to a size of about 1 mm to about 5 mm. In addition, the artery and vein were removed from the umbilical cord, and the resulting umbilical cord was cut to a size of about 1 mm to about 5 mm. Afterwards, each of the resulting placental tissue and the resulting umbilical cord was adhered to a culture dish, and cultured for 10 days to 15 days. After confirming that cells were extended from the cultured tissues, 200 U/ml of Collagenase I was added thereto for 5 hours to 6 hours, thereby isolating placenta-derived stem cells and umbilical cord-derived stem cells, respectively.

Figure 7A:
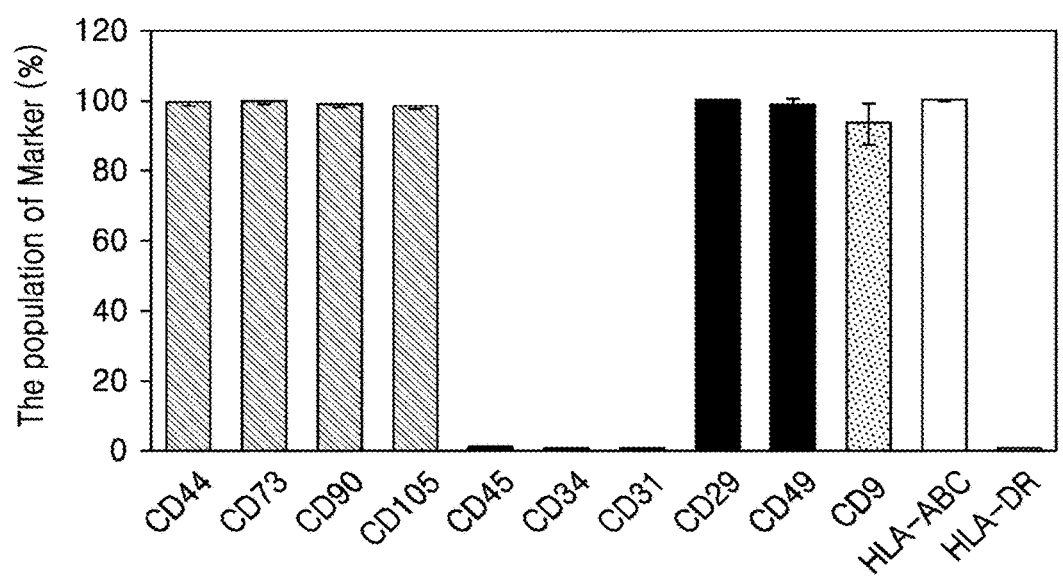
FIG. 7A shows the results of surface antigen characteristics of a placenta-derived stem cell.

To identify whether the placenta-derived stem cells exhibited the characteristics of mesenchymal stem cells, flow cytometry was performed to analyze surface proteins. The placenta-derived stem cells were washed with DPBS, added to DPBS containing 2% FBS, and then, reacted with CD44, CD73, CD90, CD105, CD45, CD34, CD31, CD29, CD49, CD9, HLA-ABC, and HLA-ER antibiotics for about 20 minutes. Subsequently, the surface antigen characteristics were analyzed by the flow cytometer (FACS Calibur, Becton Bickinson). FIG. 7A shows the results of the surface antigen characteristics of the placenta-derived stem cells. As shown in FIG. 7A, the expression levels of CD44, CD73, CD90, CD105, CD29, CD49, CD9, and HLA-ABC were high in the placenta-derived stem cells, and accordingly, it was confirmed that the placenta-derived stem cells had the characteristics of the mesenchymal stem cells.

Figure 7B:
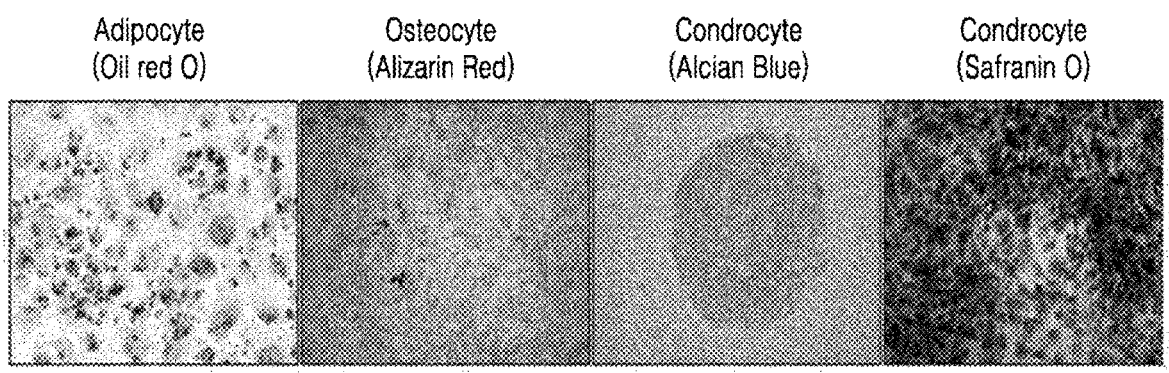
FIG. 7B is an image showing the results of inducing differentiation into adipocytes, osteocytes, and chondrocytes by adding differentiation inducers to placenta-derived stem cells.

In addition, to analyze the differentiation potency of the placenta-derived stem cells, differentiation into adipocytes, osteocytes, and chondrocytes was induced, respectively. Then, cells in a sample in which the differentiation into adipocytes was induced were stained with Oil Red O, cells in a sample in which the differentiation into chondrocytes were stained with Alcian Blue, and cells in a sample in which the differentiation into osteocytes were stained with Alizarin Red S, and the differentiation potency of the resulting cells was analyzed. FIG. 7B is an image showing the results of inducing differentiation of the placenta-derived stem cells into adipocytes, osteocytes, and chondrocytes, respectively, by adding different differentiation inducers for each differentiation of the placenta-derived stem cells. As shown in FIG. 7B, the isolated cells had the same multipotency as the mesenchymal stem cells, and accordingly, it was confirmed that the isolated cells differentiated into adipocytes, osteocytes, and chondrocytes, respectively. The isolated cells were dispensed into a multi-flask at a concentration in a range of about 100 cells/cm$^2$ to about 5,000 cells/cm$^2$. Here, the cells were at passage 0 (P0), and were subcultured over 5 passages in an MEM alpha GlutaMAX (PS-CM) medium supplemented with 25 ng/ml of fibroblast growth factor-4 (FGF-4), 1 μg/ml of heparin, 50 μg/ml of gentamicin, and 10% of fetal bovine serum (FBS) for 2 days under the culture conditions of 37□ and 5% $CO_2$.

Subsequently, to the cultured cells, a dulbecco's modified eagle medium: nutrient mixture F-12 (DMEM/F12) medium and a differentiation medium supplemented with 0.3 μM of ascorbic acid, 0.5 μg/ml of hydrocortison, and 10% of FBS were each added so that the concentration of the multi-flask became 5 M ℓ/cm$^2$, and the resulting cells were cultured for 11 days under the culture conditions of 37□ and 5% $CO_2$. For a control group, cells cultured in a medium containing no ascorbic acid and hydrocortisone were used.

Figure 1:
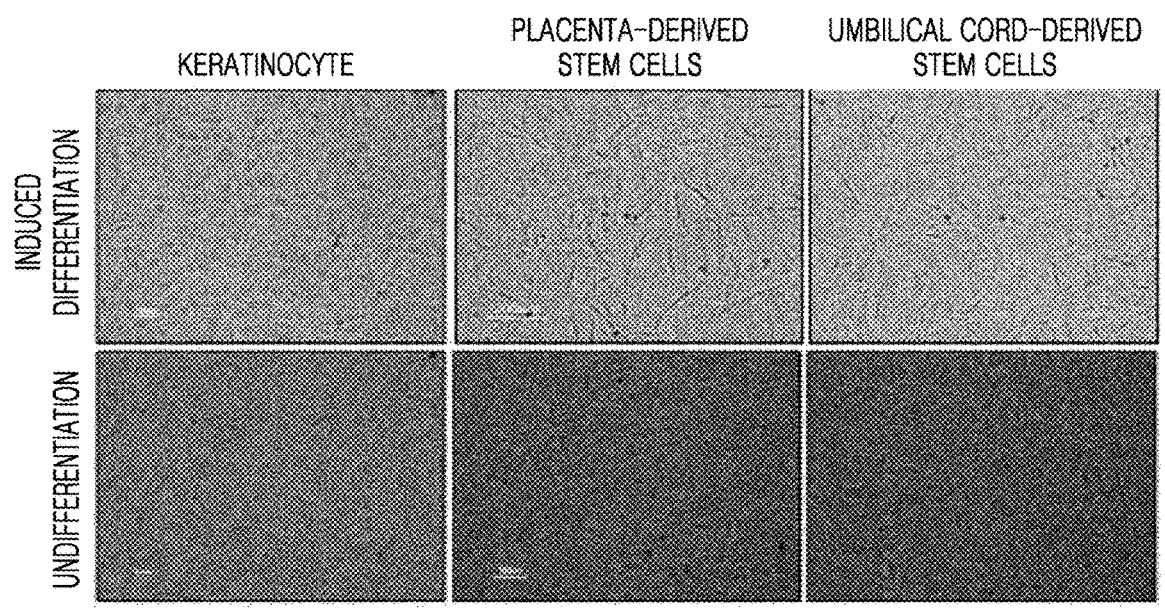
FIG. 1 shows the shape of cells including: keratinocytes after differentiation of epidermal-derived undifferentiated keratinocytes; and epidermal-derived progenitor cells after differentiation of placenta-derived stem cells and umbilical cord-derived stem cells by culturing in differentiation media for 11 days.

FIG. 1 shows the cell morphology of keratinocytes after being differentiated from epidermal-derived undifferentiated keratinocytes, and epidermal-derived progenitor cells after being differentiated from placenta-derived stem cells and umbilical cord-derived stem cells, respectively, in differentiation media for 11 days. The placenta-derived stem cells and the umbilical cord-derived stem cells each differentiated into cells in a constant size and in small and circular morphologies similar to the epidermal-derived progenitor cells. As shown in FIG. 1, it was confirmed that the placenta-derived stem cells and the umbilical cord-derived stem cells showed the morphology the epidermal progenitor cells after being cultured in the differentiation medium.

(2) Identification of Gene Expression in Differentiated Epidermal Progenitor Cells (2.1) Real-Time PCR (RT-PCR) Analysis During the process of (1) in which the placenta-derived stem cells differentiated into the epidermal progenitor cells, the expression levels of Krt5, Krt1, IVL, Krt14, and Krt10, which are genes expressed in the middle and late stages, were measured by RT-PCR.

During the process of differentiating the placenta-derived stem cells, the differentiated cells were obtained on Day 3, Day 5, Day 7, Day 9, Day 11, Day 13, Day 15, Day 17, and Day 19, and then, RNAs were extracted therefrom using phenol/chloroform. The extracted RNAs were reverse-transcribed to synthesize cDNAs. The gene expression levels of the cDNAs were analyzed by RT-PCR on the Applied Biosystems 700 sequence detection system (Foster City, CA, USA). Here, the synthesized cDNAs, a primer set specific to each of Krt5, Krt1, IVL, Krt14, and Krt10, a 2× TaqMan master mixture, and a 20× premade TaqMan gene expression analysis kit (Applied Biosystems) were used. The PCR conditions were as follows: repetition of a process of 95□ for 10 minutes, 95□ for 15 seconds, and 60□ for 1 minute1. Then, the mRNA levels of Krt5, Krt1, IVL, Krt14, and Krt10 at mRNA levels were normalized to human glyceraldehyde-3-phosphate dehydrogenase (GAPDH) levels.

TABLE 1

| Gene name | Forward primer | Reverse primer |
|---|---|---|
| Krt5 | GTC TCG CCA GTC AAG TGT GT (SEQ ID NO: 1) | GAC ACG GAG GTG AAG CTG (SEQ ID NO: 2) |
| Krt1 | GGG TGG TTA TGG TCC TGT CT (SEQ ID NO: 3) | GGA TCT CAG GGT CAA TCT CC (SEQ ID NO: 4) |

TABLE 1-continued

| Gene name | Forward primer | Reverse primer |
|---|---|---|
| IVL | CCA GGT CCA AGA CAT TCA AC (SEQ ID NO: 5) | ACT GCG GGT GGT TAT TTA TG (SEQ ID NO: 6) |
| Krt14 | GAG CAG CAG AAC CAG GAG T (SEQ ID NO: 7) | GAG AAC TGG GAG GAG GAG AG (SEQ ID NO: 8) |
| Krt10 | ACT ACT CTT CCT CCC GCA GT (SEQ ID NO: 9) | TGA GCT AAA TCC TCC ACC AA (SEQ ID NO: 10) |

Figure 2:
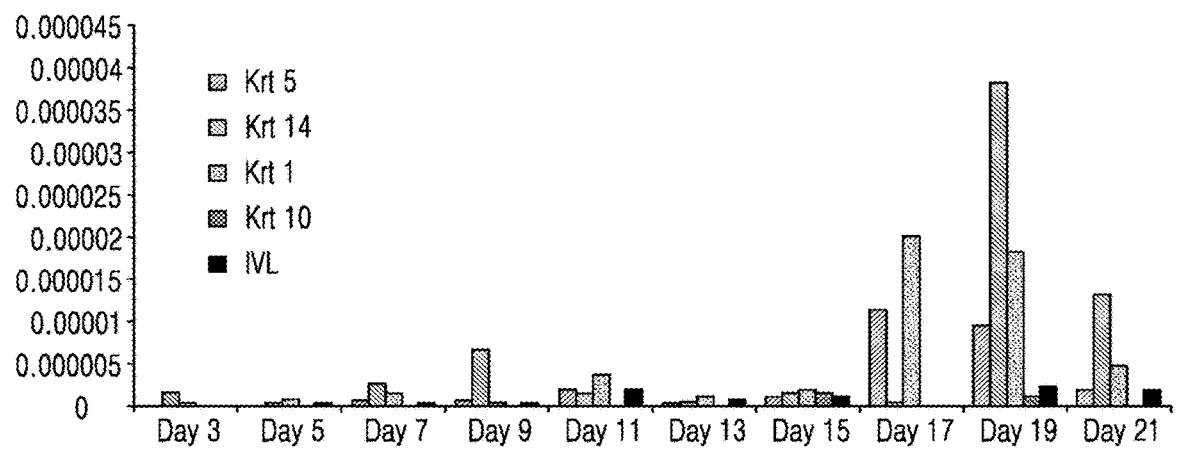
FIG. 2 shows the results of measuring expression levels of Krt5, Krt1, IVL, Krt14, and Krt10 on Day 3, Day 5, Day 7, Day 9, Day 11, Day 13, Day 15, Day 17, Day 19, and Day 21 during a process of differentiating placenta-derived stem cells into epidermal-derived progenitor cells in a differentiation medium.

FIG. 2 shows the results of measuring the expression levels of Krt5, Krt1, IVL, Krt14, and Krt10 on Day 3, Day 5, Day 7, Day 9, Day 11, Day 13, Day 15, Day 17, Day 19, and Day 21 during the process of differentiating the placenta-derived stem cells into the epidermal-derived progenitor cells in the differentiation medium. Here, the Y-axis represents the gene expression levels normalized to the human GAPDH. As shown in FIG. 2, as the differentiation proceeded, the mRNA level of Krt14, which is expressed in the middle stage of the differentiation of the epidermal progenitor cell, increased after Day 5.

(2.2) Immunoblot (IB)

During the process of (1) in which the placenta-derived stem cells differentiated into the epidermal progenitor cells, the protein level of Krt14, which is a gene expressed in the middle stage, was measured by IB.

During the process of differentiating the placenta-derived stem cells into the epidermal progenitor cells, the differentiated cells were obtained on Day 5, Day 7, Day 9, Day 11, Day 13, Day 15, Day 17, and Day 19, and then, the obtained cells were lysed in a cell lysis buffer. The cell lysis buffer contained RIPA buffer (available by Thermofisher) and protease inhibitor cocktail (available by Roche, Inc., Indianapolis, IN, USA). Proteins contained in the cell lysate were separated by 7.5% of polyacrylamide gel electrophoresis (Sodium dodecyl sulphate-polyacrylamide gel electrophoresis: SDS-PAGE). The separated proteins were transferred to a polyvinylidene fluoride (PVDF) membrane (available by EMD Millipore, Billerica, MA, USA). Then, the PVDF membrane was subjected to a reaction with a primary antibodies at a temperature of 4□ overnight. Next day, the resulting PVDF membrane was washed with a TBST solution containing Tween and Tris, and NaCl, and then, the resulting membrane was subjected to a reaction with a HRP-conjugated secondary antibody at room temperature. The protein bands were visualized using the enhanced chemiluminescence (ECL) kit system (available by EMD Millipore).

Figure 3:
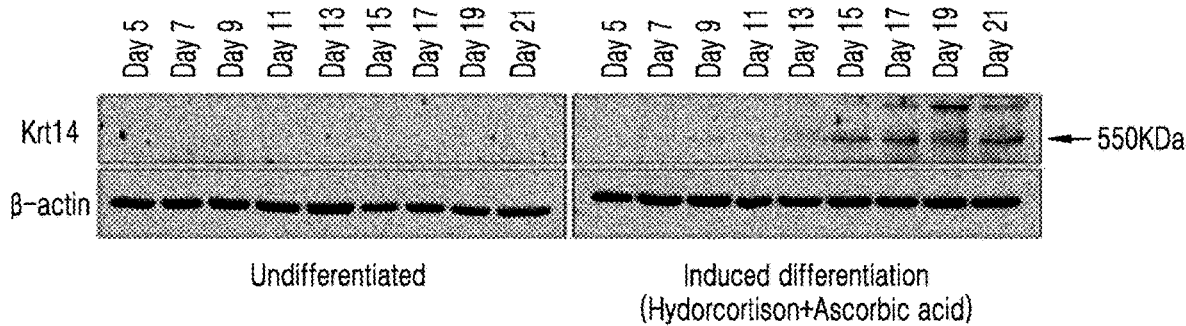
FIGS. 3 and 4 each show the results of measuring a protein level of Krt14 on Day 3, Day 5, Day 7, Day 9, Day 11, Day 13, Day 15, Day 17, Day 19, and Day 21 during a process of differentiating placenta-derived stem cells into epidermal-derived progenitor cells in a differentiation medium.
Figure 4:
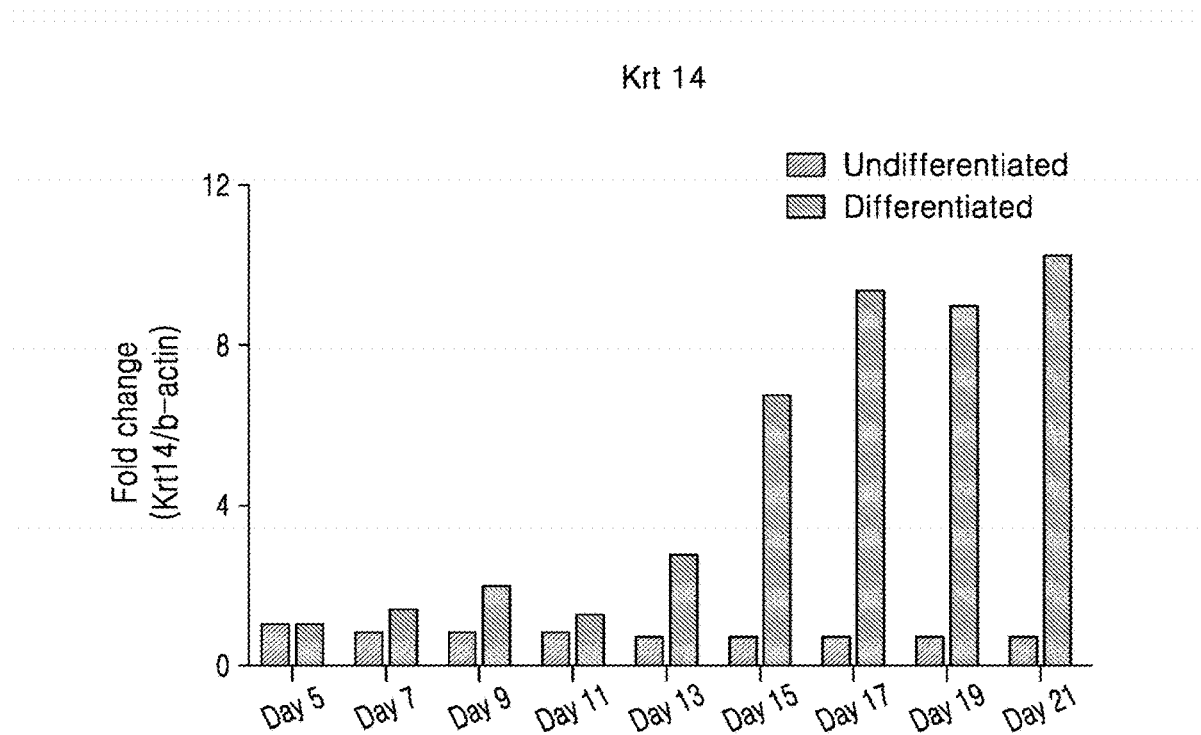

FIGS. 3 and 4 each show the results of measuring the protein level of Krt14 on Day 3, Day 5, Day 7, Day 9, Day 11, Day 13, Day 15, Day 17, Day 19, and Day 21 during the process of differentiating the placenta-derived stem cells into the epidermal-derived progenitor cells in the differentiation medium. As shown in FIGS. 3 and 4, it was confirmed that the protein level of Krt14 gradually increased from Day 5 after the placenta-derived stem cells were cultured in the differentiation medium. It was also confirmed that, after the placenta-derived stem cells were cultured in a medium containing no ascorbic acid and hydrocortisone, Krt14 was not expressed or was expressed at a very low level.

(3) Preparation of Conditioned Medium of Stem Cell-Derived Epidermal Progenitor Cell A conditioned medium was produced from the differentiated epidermal progenitor cells of (1).

Then, the differentiation medium was removed from the differentiated epidermal progenitor cells of (1), and the resulting cells were washed with DPBS to remove the remaining serum therefrom. Afterwards, a DMEM/F12 medium containing no choline chloride and phenol red was added to a culture plate so that the concentration was in a range of about 2 ml/cm$^2$ to about 3 ml/cm$^2$, and the cells were cultured for 2 days to 4 days under the culture conditions of 37□ and 5% $CO_2$. Then, the supernatant was collected from the culture of the epidermal progenitor cell mixed with the differentiated epidermal progenitor cell and the medium. Subsequently, the collected supernatant was filtered through a 0.22 μm filter to obtain the culture of the differentiated epidermal progenitor cells. For control groups, placenta-derived stem cells (hereinafter, referred to as undifferentiated stem cells) cultured in a medium containing no ascorbic acid and hydrocortisone and a conditioned medium collected by adding a medium to each of typical keratinocytes and culturing the medium.

(4) Analysis of Protein Components in Conditioned Medium of Stem Cell-Derived Epidermal Progenitor Cells The components of the cell-derived proteins in the conditioned medium of the differentiated epidermal progenitor cells obtained in (3) were identified by secretome analysis. In detail, the levels of 507 cytokines in total were identified.

The secretome analysis was performed using the RayBio™ Custom L-Series Human Cytokine Array (available from RayBiotech, Norcross, GA) according to the RayBio Human Cytokine Antibody Array protocol. The relative intensity of the obtained spots was measured by Image J, and then, corrected by the background subtraction. The results were represented as the average values of two reading results.

Figure 5:
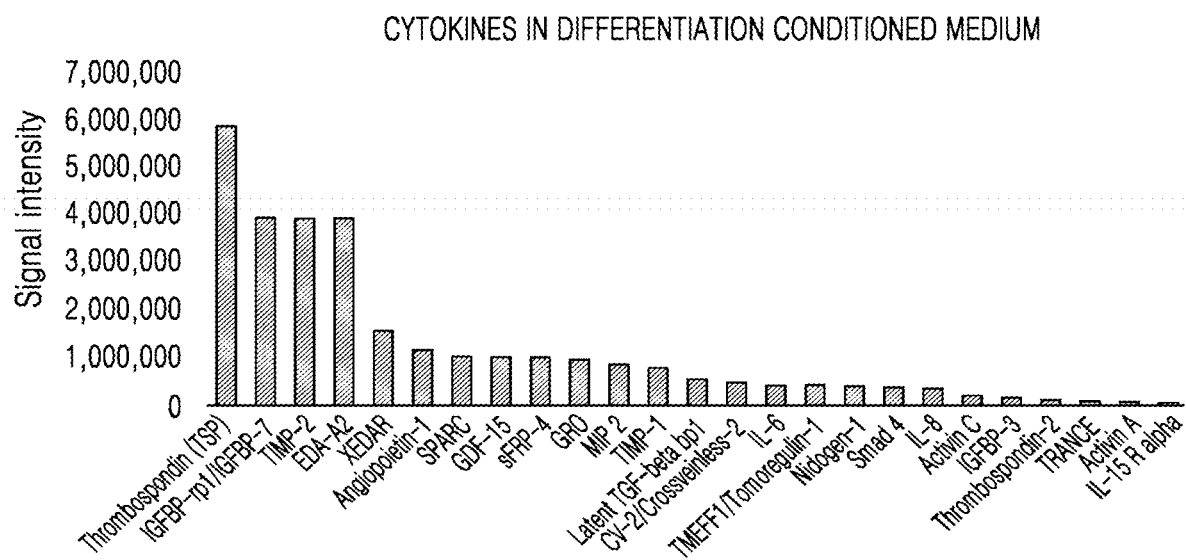
FIG. 5 shows the top 24 kinds of cytokines with high expression levels in a stem cell-derived epidermal progenitor cell conditioned medium.

FIG. 5 shows the top 24 kinds of cytokines with high expression levels in the stem cell-derived epidermal progenitor cell conditioned medium. Table 2 shows 24 cytokines expressed in large amounts in the conditioned medium of the differentiated epidermal progenitor cells. The conditioned medium of the differentiated epidermal progenitor cells may include TSP, TIMP1, TIMP2, EDA-A2, XEDAR, Angiopoietin-1, SPARC, TMEFF1/Tomoregulin-1, Nidogen-1, IGFBP-3, Thrombospondin-2, TRANCE, IL-15R alpha, and the like in large amounts.

TABLE 2

| No. | Cytokine | Signal intensity |
|---|---|---|
| 1 | Thrombospondin (TSP) | 5,886,805 |
| 2 | IGFBP-rp1/IGFBP-7 | 3,970,222 |
| 3 | TIMP-2 | 3,950,540 |
| 4 | EDA-A2 | 3,938,694 |
| 5 | XEDAR | 1,572,912 |
| 6 | Angiopoietin-1 | 1,167,638 |
| 7 | SPARC | 1,020,366 |
| 8 | GDF-3 | 1,009,469 |
| 9 | sFRP-4 | 999,123 |
| 10 | GRO | 963,242 |
| 11 | MIP 2 | 865,819 |
| 12 | TIMP-1 | 785,939 |
| 13 | Latent TGF-beta bp1 | 554,608 |
| 14 | CV-2/Crossveinless-2 | 475,676 |
| 15 | IL-6 | 441,917 |
| 16 | TMEFF1/Tomoregulin-1 | 430,143 |
| 17 | Nidogen-1 | 413,625 |
| 18 | Smad 4 | 391,810 |
| 19 | Activin C | 228,189 |
| 20 | IGFBP-3 | 182,444 |

TABLE 2-continued

| No. | Cytokine | Signal intensity |
|---|---|---|
| 21 | Thrombospondin-2 | 112,674 |
| 22 | TRANCE | 100,065 |
| 23 | Activin A | 76,102 |
| 24 | IL-15R alpha | 51,270 |

(%) Analysis of Protein Concentration in Conditioned Medium of Stem Cell-Derived Epidermal Progenitor Cells It was confirmed that the proteins listed in Table 2 were secreted in large amounts in the conditioned medium of the differentiated epidermal progenitor cells, and the secretion amount of the proteins were quantitatively analyzed by ELISA. For control groups, a conditioned medium collected by adding a new medium to the placenta-derived stem cells (hereinafter, referred to as undifferentiated stem cells) cultured a medium containing no ascorbic acid and hydrocortisone and culturing the new medium for 2 days to 4 days, and a conditioned medium collected by adding a new medium to epidermal cells and culturing the new medium for 2 days to 4 days were used. As the ELISA kit, DTP00B (available by R&D system, Minneapolis, MN) for TSP, ELH-Nidogen1 (available by Raybiotec, Norcross, Ga.) for Nidogen 1, MBS262463 (available by Mybiosource) for TRANCE, and ELH-IL15RA (available by Raybiotec, Norcross, Ga.) for IL-15R alpha were used and performed according to the manufacturer's instructions. The absorbance was measured for all cytokines by using a microplate reader Epoch (available by BioTek Inc.) at a wavelength of 450 nm, and the measured absorbance were analyzed by using the Gen5 (2.00) software.

Figure 6:
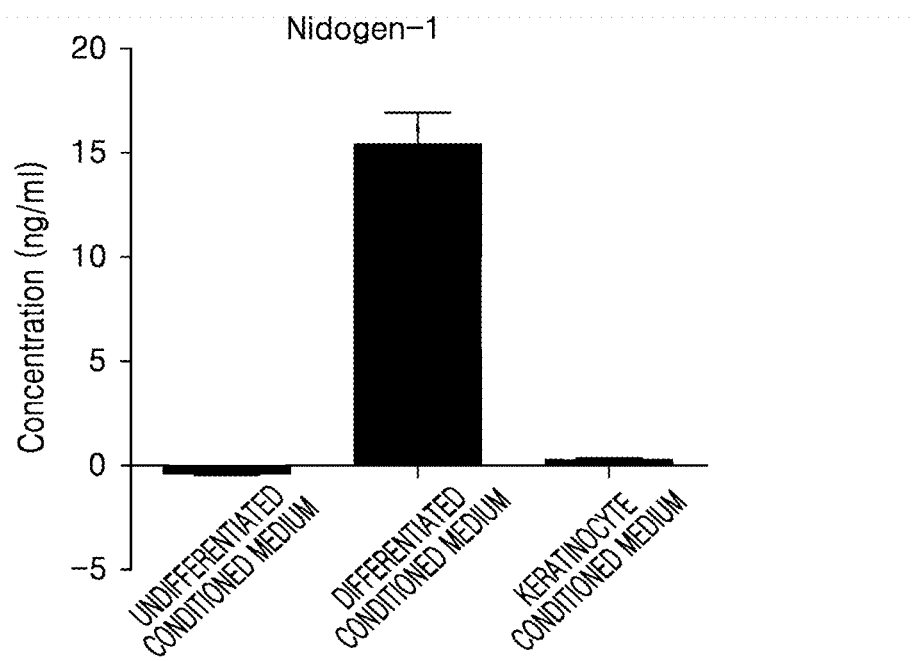
FIG. 6 shows the concentrations of Nidogen-1 in a stem cell-derived epidermal progenitor cell conditioned medium (i.e., differentiated conditioned medium), a conditioned medium of an undifferentiated stem cell (i.e., undifferentiated conditioned medium), and a typical conditioned medium of a keratinocyte (i.e., keratinocyte conditioned medium).

Table 3 shows the results of measuring the concentrations of TSP, Nidogen-1, TRANCE, and IL15R alpha in the conditioned medium of the differentiated epidermal progenitor cells. In other words, it was confirmed that the conditioned medium of the differentiated epidermal progenitor cells contained Nidogen, TSP, and the like. FIG. 6 shows the concentrations of Nidogen-1 contained in the stem cell-derived epidermal progenitor cell conditioned medium, the conditioned medium of the undifferentiated stem cells, and a typical conditioned medium of epidermal cells. As shown in FIG. 6, the amount of Nidogen-1 in the conditioned medium of differentiated epidermal progenitor cells was more than 10 times higher than that in the conditioned medium of the undifferentiated stem cells and a typical conditioned medium of epidermal cells.

TABLE 3

| No. | Cytokine | Concentration (pg/ml) | Signal intensity |
|---|---|---|---|
| 1 | TSP | 63.65 | 5,886,805 |
| 2 | Nidogen-1 | 15180 | 413,625 |
| 3 | TRANCE | 29 | 100,065 |
| 4 | IL-15R alpha | 19 | 51,270 |

The invention claimed is:

1. A method of preparing a mesenchymal stem cell-derived epidermal progenitor cell conditioned medium, the method comprising:
  differentiating placenta or umbilical cord-derived mesenchymal stem cells to mesenchymal stem cell-derived epidermal progenitor cells by culturing the stem cells in a differentiation medium containing ascorbic acid and hydrocortisone;
  producing a culture of mesenchymal stem cell-derived epidermal progenitor cells by culturing the differentiated mesenchymal stem cell-derived epidermal progenitor cells in a medium; and
  recovering the mesenchymal stem cell-derived epidermal progenitor cell conditioned medium from the culture of the stem cell-derived epidermal progenitor cells, wherein a concentration of ascorbic acid is in a range of 0.03 µM to 3 µM, and a concentration of hydrocortisone is in a range of 0.05 µg/ml to 5 µg/ml.

2. The method of claim 1, wherein the differentiating of the mesenchymal stem cells to the mesenchymal stem cell-derived epidermal progenitor cells is performed by culturing for 120 hours to 600 hours.

3. The method of claim 1, wherein the producing of the culture of the mesenchymal stem cell-derived epidermal progenitor cells is performed by culturing for 10 hours to 350 hours.

4. The method of claim 1, wherein the producing of the culture of the mesenchymal stem cell-derived epidermal progenitor cells is performed by culturing the differentiated mesenchymal stem cell-derived epidermal progenitor cells in a serum-free medium.

5. The method of claim 1, wherein the method comprises, before the differentiating of the mesenchymal stem cells to the mesenchymal stem cell-derived epidermal progenitor cells, culturing the stem cells in a serum-containing medium for 10 hours to 350 hours.

6. The method of claim 1, wherein the mesenchymal stem cell-derived epidermal progenitor cell conditioned medium comprises one or more proteins selected from Thrombospondin (TSP), Tissue Inhibitor of Metalloproteinases 1 (TIMP1), Tissue Inhibitor of Metalloproteinases 2: (TIMP2), Ectodysplasin-A2 (EDA-A2), X-linked Ectodysplasin-A Receptor (XEDAR), Angiopoietin-1, Secreted Protein Acidic and Rch in Cysteine (SPARC), Transmembrane Protein with EGF-like and Two Follistatin-like Domains 1/Tomoregulin-1 (TMEFF1/tomoregulin-1), Nidogen-1, Insulin-like Growth Factor-binding Protein-3 (IGFBP-3), Thrombospondin-2, TNF-Related Activation-Induced Cytokine (TRANCE), and Interleukin-15 receptor alpha (IL-15R alpha).

7. The method of claim 1, wherein the mesenchymal stem cell-derived epidermal progenitor cell conditioned medium comprises, at a concentration of 10 pg/ml or more, one or more proteins selected from TSP, TIMP1, TIMP2, EDA-A2, XEDAR, Angiopoietin-1, SPARC, TMEFF1/Tomoregulin-1, Nidogen-1, IGFBP-3, TRANCE, and IL-15R alpha.

8. A method of producing a protein from mesenchymal stem cell-derived epidermal progenitor cells, the method comprising:
  differentiating mesenchymal stem cells to mesenchymal stem cell-derived epidermal progenitor cells by culturing the placenta or umbilical cord-derived mesenchymal stem cells in a differentiation medium containing ascorbic acid and hydrocortisone;
  producing a culture of mesenchymal stem cell-derived epidermal progenitor cells by culturing the differentiated mesenchymal stem cell-derived epidermal progenitor cells in a medium; and
  recovering the mesenchymal stem cell-derived epidermal progenitor cell conditioned medium from the culture of the mesenchymal stem cell-derived epidermal progenitor cells, wherein a concentration of ascorbic acid is in a range of 0.03 µM to 3 µM, and a concentration of hydrocortisone is in a range of 0.05 µg/ml to 5 µg/ml.

9. The method of claim 8, wherein the differentiating of the mesenchymal stem cells to the mesenchymal stem cell-derived epidermal progenitor cells is performed by culturing for 120 hours to 600 hours.

10. The method of claim 8, wherein the producing of the culture of the mesenchymal stem cell-derived epidermal progenitor cells is performed by culturing for 10 hours to 350 hours.

11. The method of claim 8, wherein the producing of the culture of the mesenchymal stem cell-derived epidermal progenitor cells is performed by culturing the differentiated mesenchymal stem cell-derived epidermal progenitor cells in a serum-free medium.

12. The method of claim 8, wherein the method comprises, before the differentiating of the mesenchymal stem cells to the mesenchymal stem cell-derived epidermal progenitor cells, culturing the mesenchymal stem cells in a serum-containing medium for 10 hours to 350 hours.

13. The method of claim 8, wherein the protein comprises a one or more proteins selected from TSP, TIMP1, TIMP2, EDA-A2, XEDAR, Angiopoietin-1, SPARC, TMEFF1/Tomoregulin-1, Nidogen-1, IGFBP-3, TRANCE, and IL-15R alpha.

* * * * *